United States Patent [19]

Que, Jr. et al.

[11] Patent Number: 6,107,528

[45] Date of Patent: *Aug. 22, 2000

[54] IRON COMPLEXES FOR BLEACH ACTIVATION AND STEREOSPECIFIC OXIDATION

[75] Inventors: Lawrence Que, Jr., Roseville; Cheal Kim, Minneapolis, both of Minn.; Jinheung Kim, Chapel Hill, N.C.; Yan Zang, Minneapolis, Minn.

[73] Assignee: Regents of the University of Minnesota, Minneapolis, Minn.

[*] Notice: This patent is subject to a terminal disclaimer.

[21] Appl. No.: 09/204,132

[22] Filed: Dec. 2, 1998

Related U.S. Application Data

[63] Continuation of application No. 08/670,794, Jun. 21, 1996, Pat. No. 5,850,086.

[51] Int. Cl.⁷ .............................. C07C 35/08; C11D 3/00; A01N 3/00; C07F 15/00

[52] U.S. Cl. ................... 568/832; 510/311; 510/376; 8/111; 556/138; 252/186.38; 252/186.39; 252/186.4; 252/186.42; 252/186.41

[58] Field of Search ...................... 510/311, 376; 252/186.39, 186.38, 186.4, 186.41, 186.42; 556/138; 568/832; 8/111

[56] References Cited

U.S. PATENT DOCUMENTS

| | | |
|---|---|---|
| 3,200,136 | 8/1965 | Grossmith . |
| 3,332,882 | 7/1967 | Blumbergs et al. . |
| 4,128,494 | 12/1978 | Schirmann et al. . |
| 4,144,226 | 3/1979 | Crutchfield et al. . |
| 4,146,495 | 3/1979 | Crutchfield et al. . |
| 4,397,757 | 8/1983 | Bright et al. . |
| 4,412,934 | 11/1983 | Chung et al. . |
| 4,588,531 | 5/1986 | Balzer et al. . |
| 4,675,393 | 6/1987 | Coxon . |
| 4,728,455 | 3/1988 | Rerek . |
| 4,751,015 | 6/1988 | Humphreys et al. . |
| 4,871,855 | 10/1989 | Marko et al. . |
| 4,965,364 | 10/1990 | Marko et al. . |
| 5,114,611 | 5/1992 | Van Kralingen et al. . |
| 5,126,494 | 6/1992 | Gilheany et al. . |
| 5,227,543 | 7/1993 | Sharpless et al. . |
| 5,260,461 | 11/1993 | Hartung et al. . |
| 5,296,111 | 3/1994 | Suzuki et al. . |
| 5,321,143 | 6/1994 | Sharpless et al. . |
| 5,516,929 | 5/1996 | Sharpless et al. . |
| 5,580,485 | 12/1996 | Feringa et al. . |
| 5,850,086 | 12/1998 | Que et al. ................... 252/186.39 |

FOREIGN PATENT DOCUMENTS

| | | |
|---|---|---|
| 0 120 591 | 10/1984 | European Pat. Off. . |
| 0 174 132 | 3/1986 | European Pat. Off. . |
| 0 185 522 | 6/1986 | European Pat. Off. . |
| 0 284 292 | 9/1988 | European Pat. Off. . |
| 0 303 520 | 2/1989 | European Pat. Off. . |
| 0 331 229 | 9/1989 | European Pat. Off. . |
| 0 384 070 | 8/1990 | European Pat. Off. . |
| 0 392 592 | 10/1990 | European Pat. Off. . |
| 0 458 379 | 11/1991 | European Pat. Off. . |
| 0 458 396 | 11/1991 | European Pat. Off. . |
| 0 464 880 | 1/1992 | European Pat. Off. . |
| 0 537 381 | 4/1993 | European Pat. Off. . |
| 0 538 228 | 4/1993 | European Pat. Off. . |
| 0 544 490 | 6/1993 | European Pat. Off. . |
| 0 553 607 | 8/1993 | European Pat. Off. . |
| 3337921 | 5/1985 | Germany . |
| 864798 | 4/1961 | United Kingdom . |
| 907356 | 10/1962 | United Kingdom . |
| 907357 | 10/1962 | United Kingdom . |
| 1003310 | 9/1965 | United Kingdom . |
| 1519351 | 7/1978 | United Kingdom . |
| 836988 | 6/1990 | United Kingdom . |
| WO 95/07972 | 3/1995 | WIPO . |
| WO 95/34628 | 12/1995 | WIPO . |

OTHER PUBLICATIONS

National Institutes of Health Grant, *NIH Abstract No. 7R01–GM33162–01* (1983).

National Institutes of Health Grant, *NIH Abstract No. 1R01–GM38767–01* (1987).

G. Anderegg et al., "243. Pyridinderivate als Komplexbildner VIII Die Herstellung je eines neuen vier–und sechszähnigen Liganden", *Helvetica Chim. Acta.*, 50 2330–2332 (1967).

D.D. DesMarteau et al., "Mild and Selective Oxyfunctionalization of Hydrocarbons by Perfluorodialkyloxaziridines", *J. Am. Chem. Soc.*, 115 4897–4898 (1993).

Y. Dong et al., "A High–Valent Nonheme Iron Intermediate. Structure and Properties of $[Fe_2(\mu-O)_2(5-Me-TPA)_2](ClO_4)_3$," *J. Am. Chem. Soc.*, 117, 2778–2792 (1995).

B.G. Gafford et al., "Oxidative Synthesis of Bis ($\mu$–hydroxo) Chromium (III) Dimers with Aromatic Amine Ligands. Structure, Physical Properties, and Base Hydrolysis Kinetics of the Bis ($\mu$–hydroxo)bis{(tris(2–pyridylmethyl)amine)chromium(III)} Ion", *Inorg. Chem.*, 28 60–66 (1989).

J.T. Groves et al., "Aliphatic Hydroxylation Catalyzed by Iron Porphyrin Complexes", *J. Am. Chem. Soc.*, 105 6243–6248 (1983).

A.M. Khenkin et al., "Biomimetic Alkane Oxidation in the Presence of Iron Complexes", *New J. Chem.*, 13 659–667 (1989).

J. Kim, "Mechanistic Studies of Oxygen Atom Transfer at Nonheme Iron Centers", *A Thesis Submitted to the Faculty of the Graduate School of the University of Minnesota*, pp. 125–178 and 223–262 (Oct. 1995).

T. Kojima et al., "Alkane Functionalization at Nonheme Iron Centers. Stoichiometric Transfer of Metal–Bound Ligands to Alkane," *J. Am. Chem. Soc.*, 115, 11328–11335 (1993).

R. A. Leising et al., "Models for Non–Heme Iron Oxygenases: A High–Valent Iron–Oxo Intermediate," *J. Am. Chem. Soc.*, 113, 3988–3990 (1991).

(List continued on next page.)

*Primary Examiner*—Yogendra Gupta
*Assistant Examiner*—John M Petruncio
*Attorney, Agent, or Firm*—Mueting, Raasch & Gebhardt, P.A.

[57] ABSTRACT

A bleach and oxidation catalyst is provided comprising a catalytically active iron complex which can activate hydrogen peroxide or peroxy acids, for example.

9 Claims, No Drawings

OTHER PUBLICATIONS

J.R. Lindsay Smith et al., "Model Systems for Cytochrome P450 Dependent Mono–oxygenases. Part 3[1]. The Stereochemistry of Hydroxylation of cis–and trans–Decahydronaphthalene by Chemical Models for Cytochrome P450 Dependent Mono–oxygenases", *J. Chem. Soc. Perkin, Trans. II*, No. 2, 1165–1169.

R. Mello et al., "Oxidations by Methyl(trifluoromethyl)dioxirane. 2.[1] Oxyfunctionalization of Saturated Hydrocarbons", *J. Am. Chem. Soc.,* 111 6749–6757 (1989).

Müller et al., "Regio–and Stereospecific Hydroxylation of Alicyclic Hydrocarbons with Substituted Perbenzoic Acids", *Agnew Chem. Int. Engl.,* 18 407–408 (1979).

RE. Norman et al., ($\mu$–carboxylato)diiron(III) Complexes with Distinct Iron Sites. Consequences of the Inequivalence and its Relevance to Dinuclear Iron–Oxo Proteins, *J. Am. Chem. Soc.,* 112, 1554–1562 (1990).

L. Que, Jr., et al., "Modeling the Oxygen Activation Chemistry of Methane Monooxygenase and Ribonucleotide Reductase", *Acc. Chem. Res.,* 29, 190–196 (1996).

A.B. Sorokin et al., "Biomimetric Oxidation of Alkanes Under Phase Transfer Condition", *New J. Chem.,* 14 63–67 (1990).

A.M. Schwartz et al., "Surface Active Agents and Detergents", vol. I Table of Contents (pp. vii–xi) (1949), vol. II, Table of Contents (pp. vii–xv) (1959).

Y. Zang et al., "Models for Nonheme Iron Intermediates: Structural Basis for Tuning the Spin States of Fe(TPA) Complexes," *J. Am. Chem. Soc.,* 119, 4197–4205 (1997).

IRON COMPLEXES FOR BLEACH ACTIVATION AND STEREOSPECIFIC OXIDATION

This application is a continuation of Ser. No. 08/670,794 filed Jun. 21, 1996 now U.S. Pat. No. 5,850,086.

STATEMENT OF GOVERNMENT RIGHTS

The present invention was made with government support from the National Institutes of Health under Grant Nos. GM 33162 and GM 38767. The Government has certain rights in this invention.

FIELD OF THE INVENTION

The invention relates to iron complexes for use in bleach compositions, and for use in the stereospecific oxidation of organic substrates.

BACKGROUND OF THE INVENTION

Peroxide bleaching agents for use in laundering have been known for many years. Such agents are effective in removing stains, such as tea, fruit, and wine stains, from clothing at or near boiling temperatures. The efficacy of peroxide bleaching agents drop off sharply, however, at temperatures below about 60° C. To lower the temperature at which peroxide bleaching agents are effective, metal complexes capable of activation of catalysis are combined with the bleaching agents.

For example, environmentally acceptable manganese ions and complexes are known for this purpose. U.S. Pat. No. 4,728,455 discusses the use of a Mn(III)-gluconate complex as a peroxide bleach catalyst with high hydrolytic and oxidative stability. However, relatively high ratios of ligand (gluconate) to Mn are needed to obtain the desired catalytic system. Moreover, the performance of this Mn-based catalyst is inadequate when used for bleaching in the low-temperature region of about 20–40° C. Furthermore, it is restricted in its efficacy at removing a wide range of stains. EP-A-458,379 discusses a triazacyclononane-based manganese complex that displays a high catalytic oxidation activity at low temperatures, which is particularly suitable for bleaching purposes. It is believed that this improvement in bleaching activity is due to the fact that these compounds are stable under washing conditions, e.g., high alkalinity and oxidizing environment (as a result of the presence of hydrogen peroxide or peroxy acids).

In addition to the above-mentioned stain removal, dye transfer is a well-known problem in the art and has been addressed in various ways. For instance, an improved dye transfer inhibition has been obtained by using Fe-porphyrin and Fe-phtalocyanine complexes. See, for example, EP-A-537,381, EPA-553,607, EP-A-538,228.

It is well known that the stability of Fe-coordination complexes in alkaline aqueous media in the presence of peroxide compounds is very poor. This poor stability of Fe-coordination species has resulted in the necessity of very low concentrations of peroxide and, additionally, the use of polymers. See, for example, EP-A-538,228. These measures, however, only reduce the negative effects of this poor stability to some extent and do not provide a complete solution for the problem.

Improvement in activity and stability of iron compounds has been recently disclosed in WO 95 34628. By employing pentadentate ligands, the stability of the iron species has been significantly enhanced. This resulted in a catalytic system that is particularly useful for stain removal and dye bleaching in solution. Still the synthesis of the complex, and in particular of the ligand employed, leaves room for improvement. Furthermore, the remarkable anti-dye transfer properties have been obtained by using peroxyacids rather than hydrogen peroxide, which is desirable at least because of the expense associated with peroxyacids. Thus, there is a need for additional relatively stable complexes that can activate peroxy compounds in detergent compositions.

There is also a need for complexes that can stereospecifically hydroxylate hydrocarbons. The stereospecific functionalization of aliphatic C—H bonds is important in chemistry and biochemistry for drug synthesis, perfume synthesis, etc. Such transformations have been carried out by organic peroxides in a stoichiometric fashion using oxidants such as $(CF_3)_2$-dioxirane, p-$NO_2$-perbenzoic acid, and perfluorodialkyloxaziridines, on substrates such as 1,2-dimethylcyclohexane and decalin. However, the prospect of using metal complexes in combination with readily available oxidants (e.g., $O_2$, $H_2O_2$, or $ClO^-$) to carry out such reactions catalytically has aroused considerable interest in such endeavors. The latter has been inspired by the availability of metalloenzymes such as cytochrome P450, methane monooxygenase, and dopamine β-hydroxylase, which respectively utilize a heme iron, a nonheme iron, and a copper center to catalyze stereospecific hydroxylation of an alipahtic C—H bond in an enzyme active site. Iron porphyrin complexes have been successfully used as catalysts for stereospecific hydroxylation of hydrocarbons; however, the susceptibility of the porphyrin to oxidative self-degradation and the usual requirement for an expensive oxidant like PhIO have limited the utility of this approach.

There is also a need for complexes that can stereospecifically epoxidize hydrocarbons. Iron porphyrin and iron cyclam complexes have been used as catalysts for stereospecific epoxidation of C=C bonds; however, the catalysts were shown to be susceptible to oxidative self-destruction within a short period of time.

SUMMARY OF THE INVENTION

The present invention provides a class of Fe-complexes that are surprisingly stable and active toward oxidation. Advantageously and preferably, these Fe-complexes display a high catalytic oxidation activity, particularly stereospecific oxidation, when in the presence of a peroxy compound or precursor thereof. These complexes include tetradentate ligands and other ligands that are displaceable by the peroxy compound or precursor thereof. Significantly, preferred such complexes provide both favorable stain removal, remarkable dye transfer inhibition properties, and, alternatively, stereospecific oxidation of organic substrates, particularly stereospecific hydroxylation and epoxidation.

One embodiment of the present invention is an Fe-complex, or precursor thereof, having the following formula (Formula A):

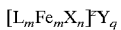

wherein:
(a) Fe is iron in the II, III, IV, or V oxidation state;
(b) X represents a coordinating species of the formula RCN, which is capable of coordinating to the Fe and being displaced by a peroxy compound or precursor thereof, wherein R is an organic group;
(c) L represents a tetradentate nontetraazamacrocyclic ligand, which is an organic molecule containing heteroatoms, capable of coordinating to the Fe through all or some of its heteroatoms;

(d) m is an integer ranging from 1 to 3;

(e) n is an integer ranging from 0 to 7;

(f) Y represents a counter ion, the type of which is dependent on the charge of the complex;

(g) z denotes the charge of the complex and is an integer which can be positive, zero, or negative; and (h) q=z/[charge Y].

A second embodiment is an Fe-complex, or precursor thereof, of the formula (Formula A):

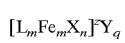

wherein:
(a) Fe is iron in the II, III, IV, or V oxidation state;

(b) X represents a coordinating species which is capable of coordinating to the Fe and being displaced by a peroxy compound or precursor thereof;

(c) L represents a tetradentate nontetraazamacrocyclic ligand, which is an organic molecule containing heteroatoms, capable of coordinating to the Fe through all or some of its heteroatoms;

(d) m is an integer ranging from 1 to 3;

(e) n is an integer ranging from 0 to 7;

(f) Y represents a counter ion, the type of which is dependent on the charge of the complex;

(g) z denotes the charge of the complex and is an integer which can be positive, zero, or negative; and (h) q=z/[charge Y].

Yet another embodiment is a detergent bleach composition prepared by combining components comprising:

(a) an Fe-complex catalyst, or precursor thereof, of the formula (Formula A):

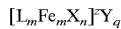

wherein:
(i) Fe is iron in the II, III, IV, or V oxidation state;

(ii) X represents a coordinating species which is capable of coordinating to the Fe and being displaced by a peroxy compound or precursor thereof;

(iii) L represents a tetradentate nonporphyrin ligand, which is an organic molecule containing heteroatoms, capable of coordinating to the Fe through all or some of its heteroatoms;

(iv) m is an integer ranging from 1 to 3;

(v) n is an integer ranging from 0 to 7;

(vi) Y represents a counter ion, the type of which is dependent on the charge of the complex;

(vii) z denotes the charge of the complex and is an integer which can be positive, zero, or negative; and (viii) q=z/[charge Y];

(b) a peroxy bleaching compound, precursor thereof, or mixtures thereof;

(c) a surface-active material; and (d) a detergency builder.

The present invention also provides methods for using the complexes of the present invention. One embodiment is a method of stereospecifically oxidizing an organic substrate comprising combining the substrate with a peroxy compound, precursor thereof, or mixtures thereof, with an oxidatively resistant Fe-complex catalyst, or precursor thereof, of the formula (Formula A):

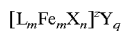

wherein:
(a) Fe is iron in the II, III, IV, or V oxidation state;

(b) X represents a coordinating species which is capable of coordinating to the Fe and being displaced by a peroxy compound or precursor thereof;

(c) L represents a tetradentate nontetraazarnacrocyclic ligand, which is an organic molecule containing heteroatoms, capable of coordinating to the Fe through all or some of its heteroatoms;

(d) m is an integer ranging from 1 to 3;

(e) n is an integer ranging from 0 to 7;

(f) Y represents a counter ion, the type of which is dependent on the charge of the complex;

(g) z denotes the charge of the complex and is an integer which can be positive, zero, or negative; and (h) q=z/[charge Y].

Another embodiment is a method of bleaching a substrate comprising contacting the substrate with a detergent bleach composition prepared by combining components comprising a peroxy compound, precursor thereof, or mixtures thereof, and an Fe-complex catalyst, or precursor thereof, of the formula (Formula A):

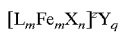

wherein:
(a) Fe is iron in the II, III, IV, or V oxidation state;

(b) X represents a coordinating species which is capable of coordinating to the Fe and being displaced by a peroxy compound or precursor thereof;

(c) L represents a tetradentate nonporphyrin ligand, which is an organic molecule containing heteroatoms, capable of coordinating to the Fe through all or some of its heteroatoms;

(d) m is an integer ranging from 1 to 3;

(e) n is an integer ranging from 0 to 7;

(f) Y represents a counter ion, the type of which is dependent on the charge of the complex;

(g) z denotes the charge of the complex and is an integer which can be positive, zero, or negative; and (h) q=z/[charge Y].

The present invention also provides compositions prepared by combining a peroxy compound, precursor thereof, or mixtures thereof with an Fe-complex of the present invention. As used herein, a peroxy compound is one that contains an O—O bond. A precursor of a peroxy compound is one that is capable of forming a peroxy compound. Thus, the term "peroxy compound precursor" includes dioxygen. A preferred group of peroxy compounds or precursors thereof include dioxygen, hydrogen peroxide, hydrogen peroxide -liberating or -generating compounds, peroxyacids and their salts, peroxyacid precursors, and mixtures thereof.

As used herein, the term "organic group" means a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As is well understood in this technical area, a large degree of substitution is not only tolerated, but is often advisable. Substitution is anticipated on the organic groups in the Fe-complexes of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

DETAILED DESCRIPTION OF THE INVENTION

Generally, the Fe-complexes of the invention may be used in compositions suitable for oxidation or bleaching comprising a peroxy compound, a precursor thereof, or mixtures thereof. The composition is suitable for use in the washing and bleaching of substrates including laundry, dishwashing and hard surface cleaning. Alternatively, the composition may be used in the textile, pharmaceutical, flavor, fine chemical industries, paper and wood pulp industries, etc., for stereospecific oxidation processes, particularly stereospecific epoxidation or hydroxylation processes.

An advantage of the Fe-complexes according to the present invention is that they generally exhibit both a high oxidation activity and a remarkably high stability in alkaline aqueous media in the presence of peroxy compounds or precursors thereof.

They also generally exhibit a high oxidation activity and a remarkably high stability in the presence of peroxy compounds or precursors thereof during stereospecific oxidation, particularly hydroxylation of aliphatic C—H bonds and epoxidation of C=C bonds. Thus, in this context, the Fe-complex catalyst is oxidatively resistant. As used herein "oxidatively resistant" means that the Fe-complex catalyst remains active after the addition of at least about 25 equivalents of $H_2O_2$ at a rate of addition of 1 equivalent per minute at room temperature to an acetonitrile solution of an organic substrate. For hydroxylation, the substrate is cis-dimethylcyclohexane, and for epoxidation the substrate is cis-stilbene. In this context "active" means that the Fe-complex catalyst continues to hydroxylate or epoxidize the substrate. Preferably, the Fe-complex catalyst remains active after the addition of at least about 50 equivalents, and more preferably after the addition of at least about 100 equivalents, and even as high as several thousand equivalents, of $H_2O_2$ under the conditions specified above.

Another advantage of the Fe-complex catalysts of the invention is that their optimal bleaching activity is observed at lower pH values (e.g., at about 6–8 pH) than those observed for the triazacyclononane-based manganese complex compounds mentioned above. This advantage may turn out to be very beneficial in view of the current tendency to shift the pH during fabric washing from highly alkaline (typically, a pH of 10) to more neutral values.

An additional advantage is that such complexes are active as dye-transfer inhibition agents as shown in Example 3. A further advantage is that hydrogen peroxide can be employed to obtain effective dye bleaching in solution, rather than more expensive peroxyacids (although peroxyacids can also be used).

Another advantage is that the complexes of the invention have a relatively low molecular weight and are, consequently, very weight-effective. Furthermore, they can be easily prepared.

A further advantage is that the complexes of the invention give rise to stereospecific oxidation, as demonstrated by the stereospecific hydroxylation of aliphatic C—H bonds and stereospecific epoxidation of C=C bonds. Stereospecific oxidation entails the oxidation of an organic substrate, with retention of its stereochemistry. This type of reaction is important in a variety of processes in the flavor and pharmaceutical industries, for example. It is envisioned that the oxidation can also be enantiospecific with the appropriate choice of chiral ligand.

The Fe-complexes of the invention can be any iron co-ordination complex of the general Formula A:

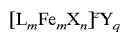

wherein:
(a) Fe is iron in the II, III, IV, or V oxidation state;
(b) X represents a coordinating species which is capable of coordinating to the Fe and being displaced by a peroxy compound or precursor thereof;
(c) L represents a tetradentate ligand, which is an organic molecule containing heteroatoms, capable of coordinating to the Fe through all or some of its heteroatoms;
(d) m is an integer ranging from 1 to 3 (preferably m is 1 or 2);
(e) n is an integer ranging from 0 to 7 (preferably n is 0 to 3);
(f) Y represents a counter ion, the type of which is dependent on the charge of the complex;
(g) z denotes the charge of the complex and is an integer which can be positive, zero, or negative; and
(h) q=z[charge Y].

Precursors of the Fe-complex of Formula A are also suitable for use in the present invention if they form the Fe-complex of Formula A under fabric washing conditions or oxidation conditions. Precursors typically include iron salts and the ligand L.

A preferred class of ligands is that of tetradentate ligands, which coordinate via four heteroatoms, such as nitrogen, oxygen, and sulfur atoms, to the Fe atom. These heteroatoms are preferably nitrogen atoms or oxygen atoms, and more preferably nitrogen atoms. The nitrogen atoms can be part of tertiary, secondary, or primary amine groups, tertiary, secondary or primary amide groups, or part of heterocyclic aromatic ring systems, e.g., pyridines, pyrazines, pyrazoles, imidazoles, benzimidazoles, thiazoles, triazoles, and pyrimidines, or combinations thereof. The oxygen atoms can be part of carboxylates, alcohols or phenols.

For certain preferred embodiments, L is a tetradentate nonporphyrin ligand. For other embodiments, L is a tetradentate nontetraazamacrocyclic ligand. As used herein, a tetradentate nontetraazamacrocyclic ligand is a tetradentate ligand that does not contain four nitrogen atoms in a ring (such as are in porphyrin and phthalocyanine). Other macrocyclic ligands, such as those containing two or three nitrogen atoms in ring, for example, that are tetradentate are within the scope of this term. Nonmacrocyclic ligands are also within the scope of this term. Furthermore, macrocyclic ligands with four heteroatoms other than nitrogen in the ring are also within the scope of this term.

Examples of suitable ligands in their unsubstituted forms are: N,N,N-tris(pyridin-2-yl-methyl)amine; N,N,N-tris(pyrazol-1-yl-methyl)amine; N,N,N-tris(imidazol-2-yl-methyl)methylamine; N,N,N-tris(benzimidazol-2-yl-methyl)methylamine; N,N,N,-tris(1,2,4-triazol-1-yl-methyl)amine; N,N,N-tris(2-amino-ethyl)amine; N,N,N-tris(2-(N,N-dimethyl)amino-ethyl)amine; (N,N-bis(pyridin-2-yl-methyl)-amino)methylphenol; (N,N-bis(pyridin-2-yl-methyl)-amino)methylcarboxylic; acid (N,N-bis(pyridin-2-yl-methyl)-amino)ethanol; and N,N'-bis(pyridin-2-yl-methyl)-ethylenediamine. Such ligands can also be substituted as long as the substituents do not adversely affect bleaching and oxidation reactions. The most preferred ligand is N,N,N-tris(pyridin-2-yl-methyl)amine, hereafter referred to as TPA.

Ligand X is a coordinating species which is capable of coordinating to the Fe and being displaced by a peroxy compound or precursor thereof. By this it is meant that, regardless of the mechanism and the actual coordinated ligand in the resultant active catalyst, ligand X is chosen such that it may be removed from the Fe center when combined with the peroxy compound or precursor thereof. Preferably, the coordinating species X is selected from the group consisting of $H_2O$, ROH, $NR_3$, RCN, $OH^-$, $RS^-$, $RO^-$, $RCOO^-$, $OCN^-$, $SCN^-$, $N_3^-$, $CN^-$, $F^-$, $Cl^-$, $Br^-$, $I^-$, $O^{2-}$, $NO_3^-$, $NO_2^-$, $SO_4^{2-}$, $SO_3^{2-}$, $PO_4^{3-}$, phenolates, alkolates or aromatic N donors such as pyridines, pyrazines, pyrazoles, imidazoles, benzimidazoles, pyrimidines, triazoles and thiazoles, and combinations thereof, wherein R is H or an organic group (preferably, an alkyl or cyclic organic group, more preferably, having 1–100 carbon atoms, and most preferably ($C_1$–$C_6$)alkyl moieties). More preferably, the coordinating species X is selected from the group consisting of $OH^-$, $H_2O$, RCN, $O^{2-}$, $NO_3^-$, $SO_4^{2-}$, aromatic N donors, and combinations thereof, wherein R is defined as above. Most preferably, X is selected from the group consisting of $OH^-$, $H_2O$, RCN, $O^{2-}$, and combinations thereof, wherein R is defined as above.

Suitable counter ions are those which give rise to the formation of storage-stable solids. Combination of the preferred iron complexes with the counter ion Y preferably involves counter ions such as $RCOO^-$, $BPh_4^-$, $ClO_4^-$, $BF_4^-$, $PF_6^-$, $RSO_3^-$, $SO_4^{2-}$, $NO_3^-$, wherein R is H or an organic group. Preferably, R is H, an alkyl or a cyclic organic group, more preferably having 1–100 carbon atoms, and most preferably ($C_1$–$C_6$)alkyl moieties. If z is positive and Y is an anion selected from the group consisting of $F^-$, $Cl^-$, $Br^-$, $I^-$, $NO_3^-$, $BPh_4^-$, $ClO_4^-$, $BF_4^-$, $PF_6^-$, $RSO_3^-$, $SO_4^{2-}$, and $CF_3SO_3^-$, wherein R is an organic group.

The Fe-complexes of the present invention can be made from a number of iron salts and tetradentate ligands. The complexes are typically prepared in the absence of oxygen by mixing equimolar amounts of iron salt and tetradentate ligand in $CH_3CN$ or $CH_3OH$, for example, adding the X component if necessary, and isolating the complex. The isolation of the complex may be accomplished by crystallization or precipitation by using a suitable counter ion Y or adding a suitable second solvent such as diethyl ether.

As previously stated, the Fe-complexes can be used to sterespecifically oxidize organic substrates. The oxidation reactions are typically carried out in the absence of oxygen by mixing a degassed solution of organic substrates (e.g., cis-dimethyl-cyclohexane) in an organic solvent such as $CH_3CN$ with the Fe-complex catalyst. To this solution is added a solution of peroxy compound or by slow addition, such as by a syringe pump at 30 µL/minute, at room temperature.

The detergent bleach composition

The bleaching composition of the invention has particular application in detergent formulations to form a new and improved detergent bleach compositions. Such detergent bleach compositions according to the present invention, include a peroxy compound or precursor thereof as defined above, the aforesaid Fe-complex catalyst having general formula (A), a surface-active material, and a detergency builder.

The Fe-complex catalyst will be present in the detergent bleach composition of the invention in amounts so as to provide the required level in the wash liquor. Generally, the Fe-complex catalyst level in the detergent bleach composition corresponds to an iron content of from about 0.0005% to about 0.5% by weight. When the dosage of detergent bleach composition is relatively low, e.g., about 1–2 g/l, the Fe content in the formulation is suitably about 0.0025% to about 0.5%, preferably about 0.005% to about 0.25% by weight. At higher product dosages, as used, e.g., by European consumers, the Fe-content in the formulation is suitably about 0.00055% to about 0.1%, preferably about 0.001% to about 0.05% by weight. Higher levels may be desired and applied in industrial bleaching processes, such as textile and paper pulp bleaching. The lower levels of the Fe-complex catalysts are preferably used in domestic laundry operations.

Detergent bleach compositions of the invention are effective over a wide pH-range of between 6 and 13, with optimal pH-range lying between 7 and 11. This is particularly advantageous as the desire for detergent bleach compositions that are effective at neutral pH increases.

The peroxy compound

The peroxy bleaching compound, i.e., the peroxy compound and precursors thereof, may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable.

Particularly preferred are sodium perborate tetrahydrate and, especially, sodium perborate monohydrate. Sodium perborate monohydrate is preferred because of its high active oxygen content. Sodium percarbonate may also be preferred for environmental reasons. The amount thereof in the composition of the invention usually will be within the range of about 5–35% by weight, preferably about 10–25% by weight.

Another suitable hydrogen peroxide generating system is a combination of a ($C_1$–$C_4$)alkanol oxidase and a ($C_1$–$C_4$) alkanol, especially a combination of methanol oxidase (MOX) and ethanol (see Example 3). Such combinations are disclosed in International Application PCT/EP 94/03003 (Unilever), which is incorporated herein by reference.

Alkylhydroxy peroxides are another class of peroxy bleaching compounds. Examples of these materials include cumene hydroperoxide and t-butyl hydroperoxide.

Organic peroxyacids may also be suitable as the peroxy bleaching compound. Such materials normally have the general formula:

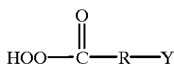

wherein R is an alkylene or substituted alkylene group containing from 1 to about 20 carbon atoms, optionally having an internal amide linkage; or a pheylene or substituted phenylene group; and Y is hydrogen, halogen, alkyl, aryl, an imido-aromatic or non-aromatic group, a COOH or

group or a quaternary ammonium group.

Typical monoperoxy acids useful herein include, for example: peroxybenzoic acid and ring-substituted peroxybenzoic acids, e.g., peroxy-α-naphthoic acid; aliphatic, substituted aliphatic and arylalkyl monoperoxyacids, e.g., peroxylauric acid, peroxystearic acid and N,N-phthaloylaminoperoxy caproic acid (PAP); and 6-octylamino-6-oxo-peroxyhexanoic acid. Typical diperoxyacids useful herein include, for example: 1,12-diperoxydodecanedioic acid (DPDA); 1,9-diperoxyazelaic acid; diperoxybrassilic acid; diperoxysebasic acid and diperoxyisophthalic acid; 2-decyldiperoxybutane-1,4-diotic acid; and 4,4'-sulphonylbisperoxybenzoic acid.

Also inorganic peroxyacid compounds are suitable, such as for example, potassium monopersulphate (MPS). If organic or inorganic peroxyacids are used as the peroxygen compound, the amount thereof will normally be within the range of about 2–10% by weight, preferably about 4–8% by weight.

All these peroxy compounds may be utilized alone or in conjunction, particularly in combination with a peroxyacid bleach precursor, and/or in combination with an organic bleach catalyst not containing a transition metal.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412, 934 and 4,675,393.

Another useful class of peroxyacid bleach precursors is that of the cationic, i.e., quaternary ammonium substituted peroxyacid precursors as disclosed in U.S. Pat. Nos. 4,751, 015 and 4,397,757, in EP-A0284292 and EP-A-331,229. Examples of peroxyacid bleach precursors of this class are: 2-(N,N,N-trimethyl ammonium) ethyl sodium-4-sulphonphenyl carbonate chloride - (SPCC); N-octyl,N,N-dimethyl-$N_{10}$-carbophenoxy decyl ammonium chloride - (ODC); 3-(N,N,N-trimethyl ammonium) propyl sodium-4-sulphophenyl carboxylate; and N,N,N-trimethyl ammonium toluyloxy benzene sulphonate.

A further special class of peroxyacid bleach precursors is formed by the cationic nitriles as disclosed in EP-A-303,520 and in European Patent Specification No.'s 458,396 and 464,880.

Any one of these peroxyacid bleach precursors can be used in the present invention, though some may be more preferred than others. Of the above classes of peroxyacid bleach precursors, the preferred classes are the esters, including acyl phenol sulphonates and acyl alkyl phenol sulphonates; the acyl-amides; and the quaternary ammonium substituted peroxyacid precursors including the cationic nitriles.

Examples of said preferred peroxyacid bleach precursors or activators are sodium-4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl-3-benzoloxy benzoate; SPCC; trimethyl ammonium toluyloxy-benzene sulphonate; sodium nonanoyloxybenzene sulphonate (SNOBS); sodium 3,5,5-trimethyl hexanoyl-oxybenzene sulphonate (STHOBS); and the substituted cationic nitriles.

Generally, the bleaching composition of the invention can be suitably formulated to contain from about 2% to about 35%, preferably from about 5% to about 25% by weight, of the peroxy compound or precursor thereof. Typically, if a peroxy compound precursor, particularly a peroxyacid precursor is used, it is used in an amount of up to about 12%, preferably about 2–10% by weight, of the composition.

As an alternative to the above described peroxy compounds, molecular oxygen may be used as the oxidant. Because dioxygen is capable of producing a peroxy compound, it is referred to herein as a peroxy compound precursor.

The surface-active material

The detergent bleach composition according to the present invention generally contains a surface-active material in an amount of from 10 to 50% by weight. Said surface-active material may be naturally derived, such as soap, or a synthetic material selected from anionic, nonionic, amphoteric, zwitterionic, cationic actives and mixtures thereof. Many suitable surface-active materials are commercially available and are fully described in the literature, for example in "Surface Active Agents and Detergents", Volumes I and II, by Schwartz, Perry and Berch.

Typical synthetic anionic surface-active materials are usually water-soluble alkali metal salts of organic sulphates and sulphonates having alkyl radicals containing from about 8 to about 22 carbon atoms, the term alkyl being used to include the alkyl portion of higher aryl radicals. Examples of suitable synthetic anionic detergent compounds are sodium and ammonium alkyl sulphates, especially those obtained by sulphating higher ($C_8$–$C_{18}$)alcohols produced, for example, from tallow or coconut oil; sodium and ammonium ($C_9$–$C_{10}$) alkyl benzene sulphonates, particularly sodium linear secondary ($C_{10}$–$C_{15}$) alkyl benzene sulphonates; sodium alkyl glyceryl ether sulphates, especially those ester of the higher alcohols derived from tallow or coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulphonates such as those derived by reacting ($C_8$–$C_{20}$) alpha-olefins with sodium bisulphite and those derived by reaction paraffins with $SO_2$ and $C_{12}$ and then hydrolysing with a base to produce a random sulphonate; sodium and ammonium ($C_7$–$C_{12}$)dialkyl sulphosccinates; and olefin sulphonates which term is used to describe material made by reacting olefins, particularly ($C_{10}$–$C_{20}$)alpha-olefins, with $SO_3$ and then neutralising and hydroysing the reaction product. The preferred anionic detergent compounds are sodium ($C_{10}$–$C_{15}$)alkylbenzene sulphonates and sodium ($C_{16}$–$C_{18}$)alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of ($C_8$–$C_{18}$)aliphatic primary or secondary linear or branched alcohols with ethylene oxide, generally 2–30 EO. Other so-called nonionic surface-active materials include alkyl polyglycosides, sugar esters, long-chain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or z,vitterionic detergent compounds are used, it is generally in small amounts in compositions based on the much more commonly used synthetic anionic and nonionic actives.

As disclosed by EP-A-544,490, the performance of the hereinbefore described bleach catalyst, may be dependent upon the active detergent system and the builder system present in the detergent bleach composition of the invention.

The detergent bleach composition of the invention will preferably comprise from 1–15% by weight of anionic surfactant and from 10–40% by weight of nonionic surfactant. In a further preferred embodiment the detergent active system is free from ($C_{16}$–$C_{12}$)fatty acids soaps.

The detergency builder

The composition of the invention normally and preferably also contains a detergency builder in an amount of from about 5–80% by weight, preferably from about 10–60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also know as Zeolite P), zeolite C, zeolite X, zeolite Y and also the zeolite P type as described in EP-A-03 84070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and the water-insoluble crystalline or amorphous aluminosilicate builder material, each of which can be used as the main builder, either alone or in admixture with minor amounts of other builders or polymers as co-builder.

It is preferred that the composition contains not more than 5% by weight of a carbonate builder, expressed as sodium carbonate, more preferable not more than 2.5% by weight to substantially nil, if the composition pH lies in the lower alkaline region of up to 10.

Other ingredients

Apart form the components already mentioned, the detergent bleach composition of the invention can contain any of the conventional additives in amounts of which such materials are normally employed in fabric witashing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilizers, such as phosphonic acid derivatives (i.e., DEQUEST types); fabric softening agents; inorganic salts and alkaline buffering agents, such as sodium sulphate, sodium silicate etc.; and usually in very small amounts, fluorescent agents; perfumes; enzymes, such as proteases, cellulases, lipases, amylases and oxidases; germicides and colourants.

When using a hydrogen peroxide source, such as sodium perborate or sodium percarbonate, as the bleaching compound, it is preferred that the composition contains not more than 5% by weight of a carbonate buffer, expressed as sodium carbonate, more preferable not more than 2.5% by weight to substantially nil, if the composition pH lies in the lower alkaline region of up to 10.

Of the additives, transition metal sequestrants, such as EDTA and the phosphonic acid derivatives, e.g., ethylene diamine tetra-(methylene phosphonate) referred to as "EDTMP," are of special importance, as not only do they improve the stability of the catalyst/$H_2O_2$ system and sensitive ingredients, such as enzymes, fluorescent agents, perfumes and the like, but also improve the bleach performance, especially at the higher pH region of above 10, particularly at pH 10.5 and above.

The invention wvill now be further illustrated by way of the following non-limiting Examples.

EXAMPLE 1

Preparation of [Fe(TPA)($CH_3CN$)$_2$]($ClO_1$)$_2$·2 $H_2O$

TPA·3$HClO_4$ was synthesized according to literature methods, as disclosed in G. Anderegg et al., *Chim. Acta.*, 50, pp. 2330–2332 (1967) and B. G. Gafford et al., *Inorg. Chem.*, 28, pp. 60–66 (1989). The synthesis of this Fe(II) complex was carried out under Ar by Schlenk line techniques. [Fe(TPA)($CH_3CN$)$_2$]($ClO_4$)$_2$. Equal mole amounts of TPA (0.29 g) and Fe($ClO_4$)$_2$·6$H_2O$ (0.36 g) were dissolved in acetonitrile. Complex [Fe(TPA)($CH_3CN$)$_2$]($ClO_4$)$_2$ was obtained as powder by adding diethyl ether to this clear solution. Recrystallization from $CH_3CN$/diethyl ether yields pure complex which gives satisfactory elemental analysis results. Yield: 0.58 g (92%). In Examples 2, 3, and 4, the above-described complex [(TPA)Fe(CH$_3$CN)$_2$](ClO$_4$)$_2$ is referred to as Fe(TPA).

Characterization: $^1$H NMR spectnim (CD$_3$CN): 10.9 ppm (pyridine;a); 8.5 and 8.4 ppm (pyridine; b); 7.3 ppm (pyridine; c); and 6.3 ppm (CH$_2$). UV-Vis (CH$_3$CN); 394 nm ($\epsilon$: 7000); 360 ($\epsilon$: 6500). Anal. Calcd for C$_{22}$H$_{24}$C$_{12}$FeN$_6$O$_8$: C, 43.13; H, 3.86; N, 13.40. Found: C, 42.87; H, 3.86; N, 12.91.

EXAMPLE 2

The bleaching activity of the Fe-catalyst prepared according to Example 1 was demonstrated in the presence hydrogen peroxide on standard tea-stained (BC-1) cotton test cloths.

The experiments were carried out at 40° C. and at a pH of 7, 8.5 and 10 in a temperature-controlled glass beaker equipped with a magnetic stirrer, thermocouple and a pH electrode. Two pieces of test cloth were stirred for 60 minutes in 1 liter of a 8.6×10$^3$ mol/l hydrogen peroxide solution in millipore water, containing concentrations of the compounds as indicated in Table 1. After rinsing with demineralised water, the test cloths were dried for 7 minutes in a microwave oven. The reflectance (R$_{460}$*) of the test cloths was measured on a Macbeth 1500/plus colour measuring system including UV-filter before and after treatment. The difference ($\Delta$R$_{460}$*) between both reflectance values thus obtained gives a measure of the bleaching performance, i.e. higher $\Delta$R$_{460}$* values correspond to an improved bleaching performance.

TABLE 1

|  | conc. (mol/l) | $\Delta$R$_{460}$* pH = 7 | $\Delta$R$_{460}$* pH = 8.5 | $\Delta$R$_{460}$* pH = 10 |
| --- | --- | --- | --- | --- |
| blank |  | 2 | 2 | 5 |
| Fe(NO$_3$)$_3$ | 5 × 10$^{-6}$ | 2 | 2 | 6 |
| Fe(TPA) | 5 × 10$^{-6}$ | 5 | 4 | 7 |

In Table 1, Fe(TPA) refers to the Fe-complex catalyst prepared according to Example 1. The blanks and Fe(NO$_3$)$_3$ experiments were used as control.

These measurements show that improved bleaching performance is obtained when Fe(TPA) is present in solution; especially around pH7–8.5.

EXAMPLE 3

The dye oxidation activity of the Fe-catalyst prepared according to Example 1 was demonstrated in the presence of hydrogen peroxide on a dye known as acid red 88.

The experiments were carried out at ambient temperature at pH=6 and 7 in a 1 cm cuvet in the presence of 8.6×10$^3$ mol/l hydrogen peroxide and 2×10$^{-4}$ mol/l acid red 88. The absorbance at 500 nm (A$_{500}$), which is the maximum of the characteristic visible absorption of the dye in aqueous media, was measured at t=0, t=5, and t=15 minutes. The ratio ($\Delta$A$_{500}$=A$_{500}$(t=5)/A$_{500}$(t=0 min)) of the absorbance at t=5 minutes and t=0 gives a measure of the dye-oxidation performance, i.e. an improved dye-oxidation performance results in reduced $\Delta$A$_{500}$ values after 5 minutes. The ratio ($\Delta$A$_{500}$=A$_{500}$(t=15)/A$_{500}$(t=0 min)) of the absorbance at t=15 minutes and t=0 gives a measure of the dye-oxidation performance, i.e. an improved dye-oxidation performance results in reduced $\Delta$A$_{500}$ values after 15 minutes. The systems without iron salt or Fe(TPA) compound do not exhibit dye oxidation under these conditions ($\Delta$A$_{500}$=1.00).

In all cases the concentration of catalyst is 5×10$^{-6}$ M.

TABLE 3

|  | time | $\Delta$A$_{500}$/pH = 6 | $\Delta$A$_{500}$/pH = 7 |
| --- | --- | --- | --- |
| Fe(NO$_3$)$_3$ | 5 minutes | 0.98 | 0.99 |
| Fe(TPA) | 5 minutes | 0.67 | 0.82 |
| Fe(NO$_3$)$_3$ | 15 minutes | 0.98 | 0.99 |
| Fe(TPA) | 15 minutes | 0.55 | 0.72 |

Fe(TPA) in Table 2 refers to the Fe-catalyst prepared according to Example 1. The experiments with Fe(NO$_3$)$_3$ were used as controls.

These measurements show that improved dye oxidation performance is obtained when Fe(TPA) is present in solution. This effect has even observed after 5 min, showing that the anti-dye transfer capabilities are quite fast.

EXAMPLE 4

The organic substrate oxidation activity of the Fe catalyst, prepared according to Example 1, was demonstrated in the presence of hydrogen peroxide or t-BuOOH on a range of organic substrates.

A degassed solution of 700 mM substrate (2.7 mL) in acetonitrile was added to 1.4 mg Fe(TPA) catalyst under argon. To this solution was added 0.3 mL of 70 mM oxidant in acetonitrile by syringe pump over 15 minutes at room temperature. The reaction solution was stirred for an additional 5 minutes to ensure complete reaction. Dichlorobenzene was added at this point as an internal standard and the solution was passed through silica gel column to remove the catalyst. The eluent was analysed by GC-MS. Results are listed in Table 4. The numbers indicated in Table 4 represent the turnovers (e.g., mol product per mol catalyst). In a blank experiment or in the presence of Fe(NO$_3$)$_3$, essentially no oxidation products could be detected.

These non-limiting examples presented in the table shows that this novel iron complex gives rise to catalyzed hydroxylation reactions and even stereospecific hydrocarbon hydroxylation reactions with hydrogen peroxide as oxidant.

TABLE 4

| oxidant | substrate | product | turnover number |
| --- | --- | --- | --- |
| H$_2$O$_2$ | cyclohexene | 2-cyclohexen-1-ol | 1.3 |
|  |  | 2-cyclohexen-1-one | 0.5 |
|  |  | cyclohene epoxide | 3 |
| H$_2$O$_2$ | cyclohexane | cyclohexanol | 3.6 |
|  |  | cyclohexanone | 0.2 |
|  |  | cyclohexene | 0.14 |
| t-BuOOH | cyclohexane | cyclohexanol | 4.5 |
|  |  | cyclohexanone | 0.2 |
|  |  | cyclohexene | 1.8 |
| H$_2$O$_2$ | cis-1,2-dimethyl-cyclohexane | 1,2-dimethyl-cyclohexene | 0.14 |
|  |  | 2,3-dimethyl-cyclohexane | 0.12 |
|  |  | cis-1,2-dimethyl-cyclohexan-1-ol | 3.6 |
|  |  | trans-1,2-dimethyl-cyclohexan-1-ol | 0.0 |
|  |  | 2,3-dimethyl-cyclohexan-1-ol and 3,4-dimethyl cyclohexan-1-ol | 1.2 |
| t-BuOOH | cis-1,2-dimethyl-cyclohexane | 1,2-dimethyl-cyclohexene | 3.2 |
|  |  | 2,3-dimethyl-cyclohexane | 0.9 |
|  |  | cis-1,2-dimethyl-cyclohexan-1-ol | 0.6 |
|  |  | trans-1,2-dimethyl-cyclohexan-1-ol | 0.4 |
|  |  | 2,3-dimethyl-cyclohexan-1-ol and 3,4-dimethyl cyclohexan-1-ol | 2.2 |

EXAMPLE 5

The organic substrate oxidation activity of the Fe catalyst, prepared according to Example 1, was demonstrated in the presence of hydrogen peroxide on a range of organic substrates.

A degassed solution of 700 mM substrate (2.7 mL) in acetonitrile was added to 2.4 mg [Fe$_2$(TPA)$_2$(O)(H$_2$O)$_2$](ClO$_4$)$_4$ catalyst under argon. To this solution was added 0.3 mL of 70 mM oxidant in acetonitrile by syringe pump over 15 minutes at room temperature. The reaction solution was stirred for an additional 5 minutes to ensure complete reaction. Dichlorobenzene was added at this point as an internal standard and the solution was passed through silica gel column to remove the catalyst. The eluent was analyzed by GC-MS. Results are listed in Table 5. The numbers indicated in Table 5 represent the turnovers (eg mol product per mol catalyst). In a blank experiment or in absence of the catalyst [Fe$_2$(TPA)$_2$(O)(H$_2$O)$_2$](ClO$_4$)$_4$, essentially no oxidation products could be detected.

These non-limiting examples presented in the table shows that this novel iron complex gives rise to catalyzed hydroxylation reactions and even stereospecific hydrocarbon hydroxylation reactions with hydrogen peroxide as oxidant.

TABLE 5

| oxidant | substrate | product | turnover number |
|---|---|---|---|
| H$_2$O$_2$ | cyclohexane | cyclohexanol | 2.40 |
| | | cyclohexanone | 0.85 |
| | | cyclohexene | 0.12 |
| | cyclooctane | cyclooctanol | 2.40 |
| | | cyclooctanone | 1.10 |
| | | cyclooctene | 0.47 |
| | cis-dimethyl-cyclohexane | 1,2-dimethyl-cyclohexene | 0.12 |
| | | 2,3-dimethyl-cyclohexene | 0.10 |
| | | cis-1,2-dimethyl-cyclohexan-1-ol | 2.60 |
| | | trans-1,2-dimethyl-cyclohexan-1-ol | 0.0 |
| | | 2,3-dimethyl-cyclohexan-1-ol and 3,4-dimethyl-cyclohexan-1-ol | 0.90 |
| | trans-dimethyl-cyclohexane | 1,2-dimethyl-cyclohexene | trace |
| | | 2,3-dimethyl-cyclohexene | 0.13 |
| | | cis-1,2-dimethyl-cyclohexan-1-ol | 0.0 |
| | | trans-1,2-dimethyl-cyclohexan-1-ol | 0.90 |
| | | 2,3-dimethyl-cyclohexan-1-ol and 3,4-dimethyl-cyclohexan-1-ol | 1.3 |
| | cis-stilbene | cis-stilbene oxide | 1.2 |
| | | trans-stilbene oxide | trace |
| | | benzaldehyde | 0.7 |
| | | meso-hydrobenzoin | 1.0 |

All patents, patent documents, and publications cited herein are incorporated by reference as if individually incorporated. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of stereospecifically oxidizing an organic substrate comprising combining the substrate with a peroxy compound, precursor thereof, or mixtures thereof, and with an oxidatively resistant Fe-complex catalyst, or precursor thereof, of the formula:

$\{L_mFe_mX_n\}^zY_q$ wherein:
(a) Fe is iron in the II, II, IV, or V oxidation state;
(b) X represents a coordinating species which is capable of coordinating to the Fe and being displaced by a peroxy compound or precursor thereof;
(c) L represents a tetradentate noxtetraazamacrocyrclic ligand, which is an organic molecule containing heteroatoms, capable of coordinating to the Fe through all or some of its heteroatoms;
(d) m is an integer ranging from 1 to 3;
(e) n is an integer ranging from 0 to 7;
(f) Y represents a counter ion, the type of which is dependent on the charge of the complex;
(g) z denotes the charge of the complex and is an integer which is positive, zero, or negative; and
(h) q=z/{charge Y}.

2. The method of claim 1 wherein when the organic substrate is cis-dimethyl-cylcohexane, the peroxy compound and Fe-complex catalyst provide a conversion efficiency of at least 26% for cis-dimethyl-cyclohexane to cis-1,2-dimethyl-cyclohexan-1-ol.

3. The method of claim 1, wherein:
(a) X is selected from the group consisting of OH$_3$ H$_2$O, O$^{2-}$, and combinations thereof;
(b) the tetradentate ligand is N,N,N-tris(pyridin-2-yl-methyl)amine; and
(c) m is 1 or 2.

4. A method of stereospecifically oxidizing an organic substrate comprising combining the substrate with a peroxy compound, precursor thereof, or mixtures thereof, and with an oxidatively resistant Fe-complex catalyst, or precursor thereof, of the formula:

$\{L_mFe_mX_n\}^zY_q$ wherein:
(a) Fe is iron in the II, III, IV, or V oxidation state;
(b) X represents a coordinating species which is capable of coordinating to the Fe and being displaced by a peroxy compound or precursor thereof;
(c) L represents a tetradentate noxtetraazamacrocyrclic ligand, which is an organic molecule containing heteroatoms, capable of coordinating to the Fe through all or some of its heteroatoms;
(d) m is an integer ranging from 1 to 3;
(e) n is an integer ranging from 0 to 7;
(f) Y represents a counter ion, the type of which is dependent on the charge of the complex;
(g) z denotes the charge of the complex and is an integer which is positive, zero, or negative; and
(h) q=z/{charge Y};
wherein the Fe-complex catalyst is capable of cis-dihydroxylation of a C=C bond.

5. A method of stereospecifically oxidizing an organic substrate comprising combining the substrate with a peroxy compound, precursor thereof, or mixtures thereof, and with an oxidatively resistant Fe-complex catalyst, or precursor thereof, of the formula:

$\{L_mFe_mX_n\}^zY_q$ wherein:
(a) Fe is iron in the II, III, IV, or V oxidation state;
(b) X represents a coordinating species which is capable of coordinating to the Fe and being displaced by a peroxy compound or precursor thereof;
(c) L represents a tetradentate noxtetraazamacrocyrclic ligand, which is an organic molecule containing heteroatoms, capable of coordinating to the Fe through all or some of its heteroatoms;
(d) m is an integer ranging from 1 to 3;
(e) n is an integer ranging from 0 to 7;
(f) Y represents a counter ion, the type of which is dependent on the charge of the complex;

(g) z denotes the charge of the complex and is an integer which is positive, zero, or negative; and (h) q=z/{charge Y};

wherein the Fe-complex catalyst is capable of stereospecifically epoxidizing a C=C bond.

6. The method of claim 1 wherein the Fe-complex catalyst is capable of stereospecifically hydroxylating an aliphatic C—H bond.

7. The method of claim 1 wherein the peroxy compound is $H_2O_2$.

8. The method of claim 4 wherein the peroxy compound is $H_2O_2$.

9. The method of claim 5 wherein the peroxy compound is $H_2O_2$.

\* \* \* \* \*

UNITED STATES PATENT AND TRADEMARK OFFICE
CERTIFICATE OF CORRECTION

PATENT NO.    : 6,107,528
DATED         : August 22, 2000
INVENTOR(S)   : Que, Jr. et al.

It is certified that error appears in the above-identified patent and that said Letters Patent is hereby corrected as shown below:

Column 8,
Line 38, please delete "WVhen" and insert -- When --;

Column 9,
Line 60, please delete "1,246,339";

Column 11,
Line 29, please delete "z,vitterionic" and insert -- zwitterionic --;

Column 12,
Line 20, please delete "witashing" and insert -- washing --;

Column 15,
Line 64, please delete "noxtetraazamacrocyrclic" and insert -- nontetraazamacrocyclic --;

Column 16,
Line 15, please delete "OH$_3$" and insert -- OH, --;
Line 33, please delete "noxtetraazamacrocyrclic" and insert -- nontetraazamacrocyclic --;
Line 60, please delete "noxtetraazamacrocyrclic" and insert -- nontetraazamacrocyclic --;

Signed and Sealed this

Twenty-third Day of October, 2001

*Attest:*

Nicholas P. Godici

NICHOLAS P. GODICI
*Attesting Officer*       *Acting Director of the United States Patent and Trademark Office*